United States Patent [19]

Yamamoto

[11] Patent Number: 5,618,283
[45] Date of Patent: Apr. 8, 1997

[54] SANITARY NAPKIN

[75] Inventor: Masamitsu Yamamoto, Kawanoe, Japan

[73] Assignee: Uni-Charm Corporation, Ehime-ken, Japan

[ * ] Notice: The term of this patent shall not extend beyond the expiration date of Pat. No. 5,413,569.

[21] Appl. No.: 359,380

[22] Filed: Dec. 20, 1994

Related U.S. Application Data

[63] Continuation of Ser. No. 151,426, Nov. 15, 1993, Pat. No. 5,413,569.

[30] Foreign Application Priority Data

Nov. 17, 1992 [JP] Japan .................................. 4-079168

[51] Int. Cl.⁶ .................................................. A61F 13/15
[52] U.S. Cl. ........................... 604/390; 604/387; 604/389
[58] Field of Search .................................. 604/386, 387, 604/385.2, 369, 390

[56] References Cited

U.S. PATENT DOCUMENTS

| | | | |
|---|---|---|---|
| 4,315,507 | 2/1982 | Whitehead et al. | |
| 4,701,175 | 10/1987 | Boland et al. | 604/387 |
| 4,822,435 | 4/1989 | Igaue . | |
| 5,037,415 | 8/1991 | Leroy et al. | 604/386 |
| 5,074,856 | 12/1991 | Coe et al. | 604/385.2 |
| 5,133,704 | 7/1992 | Wheeler . | |
| 5,154,715 | 10/1992 | Van Iten | 604/386 |
| 5,275,591 | 1/1994 | Mavinkurve | 604/387 |
| 5,429,630 | 7/1995 | Beal et al. | 604/387 |
| 5,429,633 | 7/1995 | Davis et al. | 604/387 |
| 5,460,624 | 10/1995 | Ahr et al. | 604/387 |

FOREIGN PATENT DOCUMENTS

| | | |
|---|---|---|
| 0268858 | 6/1988 | European Pat. Off. . |
| 0301491 | 2/1989 | European Pat. Off. . |
| 0557047 | 8/1993 | European Pat. Off. . |
| 2233235 | 1/1991 | United Kingdom . |
| 2264645 | 9/1993 | United Kingdom . |
| 92/07536A | 5/1992 | WIPO . |
| 9207536 | 5/1992 | WIPO . |
| 10733 | 6/1993 | WIPO ................... 604/385.2 |
| 12135 | 6/1994 | WIPO ................... 604/385.2 |

*Primary Examiner*—Michael J. Milano
*Attorney, Agent, or Firm*—Lowe, Price, LeBlanc & Becker

[57] ABSTRACT

The present invention provides a sanitary napkin which includes a side barrier incorporating an elastic member disposed on each side of the sanitary napkin, and a separate wing portion disposed outwardly of each side barrier, so that the wing portions can be folded onto the outer side of the crotch portion of an undergarment.

5 Claims, 2 Drawing Sheets

SANITARY NAPKIN

This application is a continuation of application Ser. No. 08/151,426 filed Nov. 15, 1993, now U.S. Pat. No. 5,413,569.

BACKGROUND OF THE INVENTION

The present invention generally relates to a sanitary napkin or a sanitary pad for absorbing and retaining menses, more particularly to a sanitary napkin having wing portions which encircle the crotch portion of an undergarment for attaching the napkin thereto.

There exist different types of sanitary napkin constructions in the prior art. One type of construction has a liquid permeable topsheet, a liquid impermeable backsheet and an absorbent core interposed between the topsheet and the backsheet. The backsheet and the topsheet co-extend outwardly from each side edge of a longitudinal middle portion of the absorbent core to form wing portions. When a sanitary napkin of such construction is put into use, each of the wing portions is folded outwardly toward the back face of an undergarment crotch portion, and is attached thereto by means of adhesives applied onto the back face of the wing portions. This type of construction therefore is advantageously effective in attaching the sanitary napkin firmly to the undergarment crotch portion.

Another type of construction has a side barrier which extends longitudinally along each side of a sanitary napkin. The side barrier has an elastic member so that the side barrier is spaced away or stands upwardly from the top surface of the sanitary napkin as the elastic member elastically contracts. The side barrier is advantageously effective in preventing side leakage of body fluid.

However, no prior art has or discloses a construction which incorporates both of the features as described above. Accordingly, conventional sanitary napkin constructions fail to effectively prevent side leakage of body fluid or to firmly attach the sanitary napkin to the undergarment crotch portion.

Therefore, it would be desirable to provide a sanitary napkin which incorporates the advantageous features that each of the former and latter napkin constructions individually has.

SUMMARY OF THE INVENTION

In accordance with the present invention, there is provided a sanitary napkin which comprises a liquid permeable topsheet having opposite side edges, a liquid impermeable backsheet and an absorbent core interposed between the topsheet and the backsheet. The sanitary napkin further comprises a wing portion extending laterally outwardly from each side edge of the absorbent core, and a fastener disposed at least on the back face of the wing portion for attaching the wing portion to an undergarment.

Each of the side edges of the topsheet extends from the top face toward the back face of the absorbent core for securement thereof to the backsheet so that the topsheet surrounds the respective side edges of the absorbent core. The topsheet is spaced outwardly from each side edge of the absorbent core at least along a proximal edge of the respective wing portion to define a sleeved, side barrier that extends outwardly from the side edge of the absorbent core. Each of the side barriers incorporates an elastic member which extends longitudinally along a distal edge of the side barrier, so that the side barrier stands up by the contracting force of the elastic member.

In a particular embodiment of the present invention, the wing portion extends laterally outwardly from a middle section of the absorbent core. The topsheet is illustrated to completely surround the absorbent core. The fastener may comprise adhesives applied onto the back face of the wing portion.

When in use, an underface of the napkin is placed on the inner face of a crotch portion of an undergarment. Each of the wing portions can be folded outwardly onto the outer face of the crotch portion for securement thereto by a fastener. The side barrier then stands up by contracting force of the elastic member to snugly fit to a user's skin, without the side barrier falling outwardly by the influence of the folded wing portion.

Numerous other features and advantages of the present invention will become readily apparent from the following detailed description, the accompanying drawings, and the appended claims.

PREFERRED EMBODIMENTS OF THE INVENTION

Figure 1:
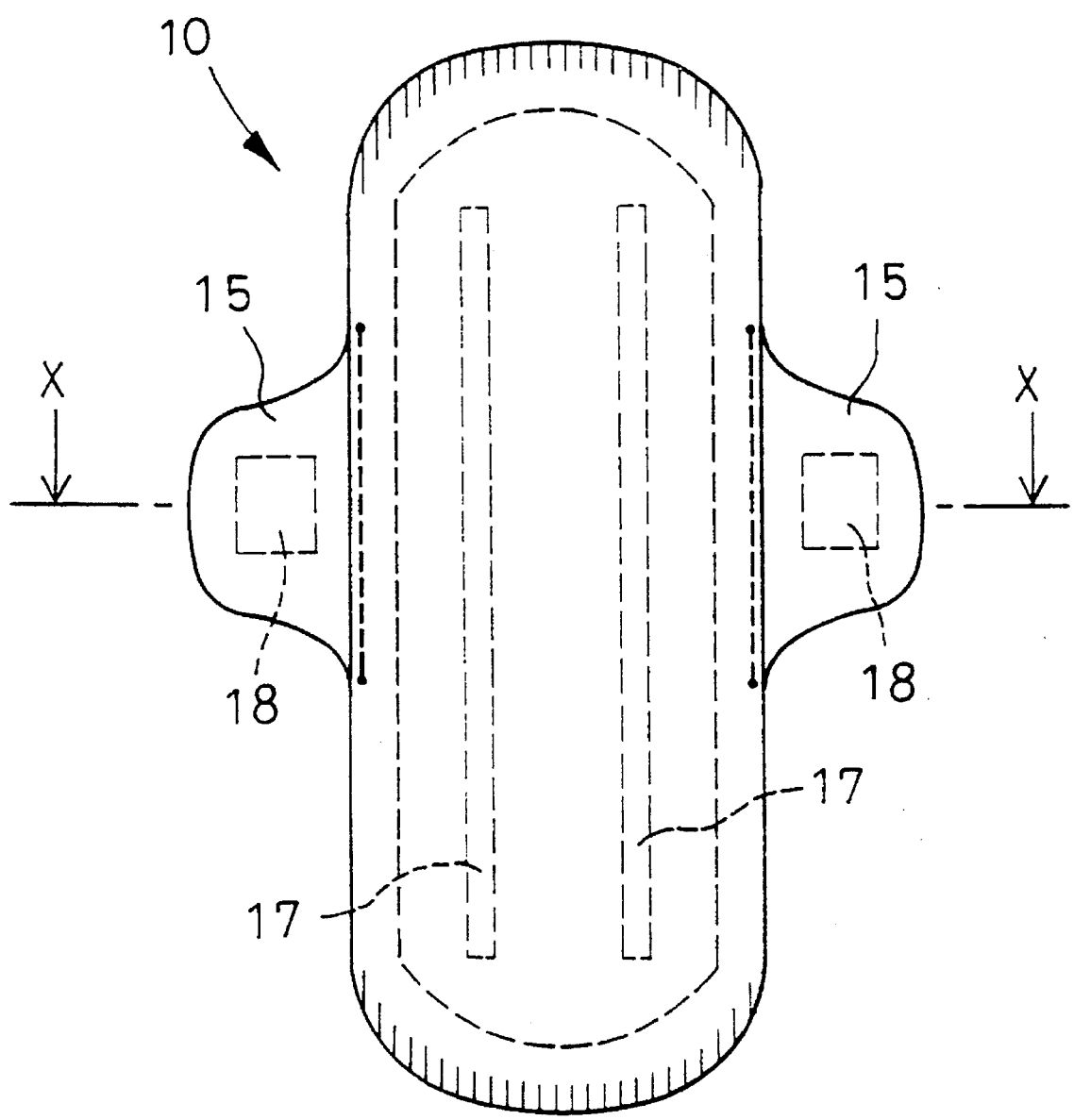
FIG. 1 is a plan view of a sanitary napkin embodying the principles of the present invention.

While the present invention is susceptible of embodiments in various forms, there is shown in the drawing and will hereinafter be described in detail a specific embodiment thereof, with the understanding that the present disclosure is to be considered as an exemplification of the principles of the invention, and is not intended to limit the invention to the specific embodiment illustrated.

Figure 2:
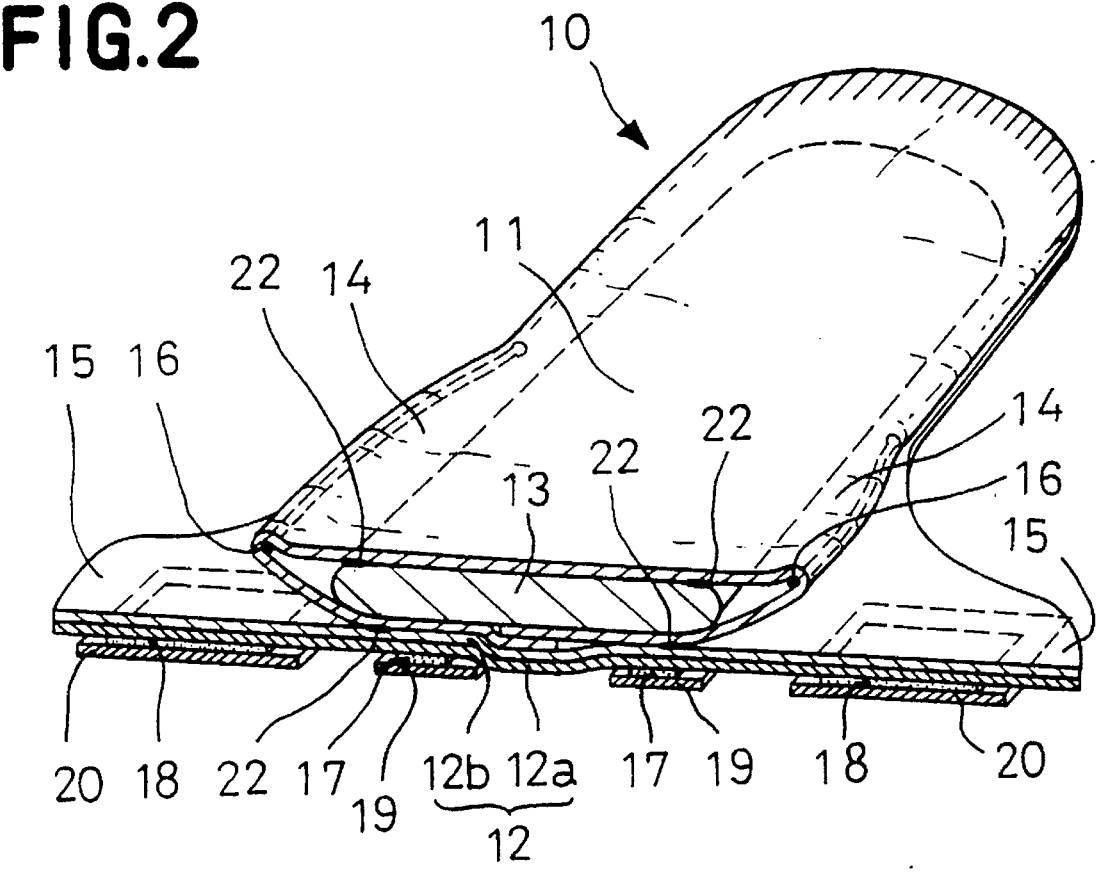
FIG. 2 is a perspective cut-away view of the sanitary napkin, illustrating an enlarged cross-section taken along lines X—X of FIG. 1; and, FIG. 3 is an enlarged cross-sectional view, illustrating another embodiment of a wing portion.

Referring now to FIGS. 1 and 2, there is illustrated a sanitary napkin 10 embodying the principles of the present invention. The sanitary napkin 10 has a liquid permeable topsheet 11, a liquid impermeable backsheet 12 and an absorbent core 13 interposed between the topsheet 11 and the backsheet 12. The absorbent core 13 is configured to have smaller width and length dimensions than the topsheet 11 and the backsheet 12. The sanitary napkin 10 further has a side barrier 14 which is positioned forwardly toward the front end of the sanitary napkin 10 and extends outwardly from each side thereof. A wing portion 15 is disposed outwardly of each of the side barriers 14, and extends outwardly from the respective side of the sanitary napkin 10.

In the illustrated embodiment, the side barrier 14 comprises a sleeve portion constructed by a portion of the topsheet 11. Specifically, the topsheet 10 extends from the top face of the absorbent core 13 toward the back face thereof to encircle the absorbent core 13. As best seen in FIG. 2, between the top and back faces of the absorbent core 13, the topsheet 11 extends outwardly of each side edge of the absorbent core 13 at least along the proximal edge of the wing portion 15 so that the topsheet portion is spaced outwardly from the side edge of the absorbent core 13 to define the sleeved, side barrier 14.

The side barrier 14 encloses an elastic member 16 within its sleeve. In this embodiment, the elastic member 16 extends longitudinally along the distal edge of the side barrier 14, and is at least at its opposite ends attached to an inner face of the side barrier 14 in its stretched condition. The side barrier 14 has its proximal edge integrally connected to the absorbent core 13 and the backsheet 12 by respective adhesives 22. Accordingly, the side barrier 14 is configured to maintain its width dimension extending outwardly from the proximal edge thereof, and its inner volume enclosed by the sleeve thereof.

Although the side barrier 14 comprises a part of the liquid permeable topsheet 11 in this embodiment, the side barrier 14 may be rendered hydrophobic or liquid-impermeable, when desired, by suitable treatment.

A lateral spacing of the respective distal edges of the opposite side barriers 14 of the sanitary napkin 10 is suitably dimensioned to be greater than the width of a crotch portion of an undergarment (or a sanitary undergarment), so that the distal edge of each side barrier 14 extends a proper distance outwardly from the respective outer edge of the undergarment crotch portion. This dimensioning desirably abates side leakage of menses. However, the foresaid lateral spacing may be suitably dimensioned for the distal edge of each side barrier 14 so as not to extend outwardly from the respective outer edge of the foresaid crotch portion.

In FIG. 2, the backsheet 12 is illustrated to comprise a liquid impermeable sheet 12a laminated onto a liquid permeable sheet 12b. The backsheet 12 may comprise the liquid impermeable sheet 12a only. Alternatively, the liquid permeable sheet 12b may be replaced by another liquid impermeable sheet.

A pair of laterally spaced, parallel lines or bands of adhesives 17 is disposed to extend longitudinally on the central lower surface of backsheet 12. A rectangularly shaped adhesive 18 is placed on the central lower surface of each of the wing portions 15. These adhesives 17, 18 are respectively covered by release sheers 19, 20 for protection thereof.

Figure 3:
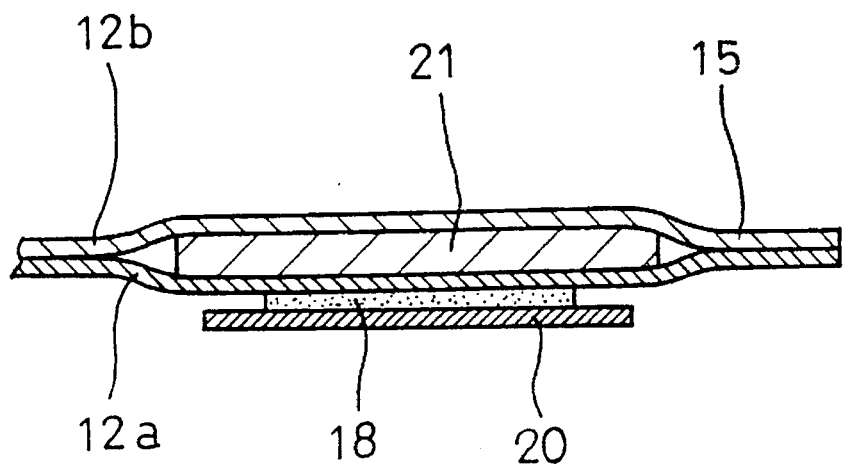

As illustrated in FIG. 3, a reinforcing piece 21 is integrally interposed between the two sheets 12a, 12b of the wing portion 15. The reinforcing piece 21 is sized to be slightly larger than a wing portion area where the adhesives 18 is placed, and is positioned over the wing portion area. The reinforcing piece 21 has rigidity greater than that of either one of the sheets 12a, 12b or that of the laminated combination thereof. Accordingly, such construction helps prevent occurrence of the undesirable situation that the wing portion 15 adheres onto itself through the adhesives 18 when it is wrinkled or twisted during application procedures by a user. The reinforcing piece 21 may be integrally attached onto the lower surface of the sheet 12a, although not shown in the drawings. Then, the adhesives 18 may be conveniently disposed on an exposed surface of the reinforcing piece 21.

A user can apply the sanitary napkin 10 to an undergarment by first removing the release sheets 19 to expose the adhesives 17. Then the central section of the sanitary napkin 10 is pressed onto an inner surface of the undergarment crotch portion so that the central section is adhered to the inner surface through the adhesives 17. The user now removes the release sheets 20 to expose the adhesives 18, and folds each wing portion 15 outwardly onto an outer surface of the crotch portion to adhere each wing portion 15 to the outer surface through the adhesives 18. When the sanitary napkin 10 is completely attached to the undergarment, each of the side barriers 14 stands up by the contracting force of the respective elastic member 16. Since the side barrier 14 is configured to be separated from the respective wing portion 15, when the wing portion 15 is folded onto the outer side of the undergarment crotch portion for securement thereto, the folding does not act to drag the side barrier 15 outwardly.

Various materials as known in the art may be utilized to construct elements of the sanitary napkin 10 of the present invention. For example, the topsheet 11 may comprise a non-woven fabric or an apertured plastic film. The sheets 12a, 12b may comprise a plastic film and a hydrophobic non-woven fabric, respectively.

From the foregoing, it will be observed that numerous modifications and variations can be effected without departing from the true spirit and scope of the novel concept of the present invention. It will be appreciated that the present disclosure is intended as an exemplification of the invention, and is not intended to limit the invention to the specific embodiment illustrated. The disclosure is intended to cover by the appended claims all such modifications as fall within the scope of claims.

What is claimed is:

1. A sanitary napkin comprising
  (a) an absorbent core having a top surface, a bottom surface and two laterally spaced apart sides,
  (b) a topsheet comprising a liquid-permeable sheet
    (1) that substantially entirely surrounds said absorbent core,
    (2) that is in direct face-to-face contact with both said top and bottom surfaces of said absorbent core, and
    (3) that extends laterally outwardly a spaced distance away from said absorbent core sides so as to form two laterally spaced apart sleeve portions,
  (c) an elastic member in a stretched condition extending along the interior of each of said sleeve portions so that each sleeve portion stands up and forms a side barrier,
  (d) a liquid-impermeable backsheet
    (1) that is bonded to the portion of said topsheet that is in direct face-to-face contact with said bottom surface of said absorbent core,
    (2) that has two spaced apart wing portions that are separate from said sleeve portions, each wing portion extending laterally outwardly with respect to each said absorbent core side, each wing portion having a top face and a back face, and
  (e) a fastener on said back face of each said wing portion which permits attachment of said wing portion to the outer surface of the crotch portion of an undergarment.

2. The sanitary napkin of claim 1, wherein each said wing portion is provided with a reinforcing piece which has a rigidity greater than that of the backsheet forming said wing portion and which is attached to said wing portion.

3. A sanitary napkin of claim 2, wherein said reinforcing piece is sized to be larger than the size of the wing portion area where said fastener is placed.

4. A sanitary napkin according to claim 1, wherein said absorbent core sides are not in complete direct face-to-face contact with said topsheet.

5. A sanitary napkin according to claim 1, each said sleeve portion establishes an open space between the interior of said topsheet and each of said absorbent sides.

* * * * *